US00PP31477P3

(12) United States Plant Patent
Joseph

(10) Patent No.: US PP31,477 P3
(45) Date of Patent: Feb. 25, 2020

(54) ***HUMULUS YUNNANENSIS* PLANT NAMED 'KRIYA'**

(50) Latin Name: ***Humulus yunnanensis* var *kriya***
Varietal Denomination: Kriya

(71) Applicant: Bomi, LLC, Los Gatos, CA (US)

(72) Inventor: Bomi Joseph, Los Gatos, CA (US)

(73) Assignee: BOMI, LLC, Reno, NV (US)

( * ) Notice: Subject to any disclaimer, the term of this patent is extended or adjusted under 35 U.S.C. 154(b) by 0 days.

(21) Appl. No.: 15/932,529

(22) Filed: Mar. 12, 2018

(65) Prior Publication Data

US 2019/0281744 P1 Sep. 12, 2019

(51) Int. Cl.

| | |
|---|---|
| ***A01H 5/02*** | (2018.01) |
| ***A01H 6/00*** | (2018.01) |
| ***A01H 6/28*** | (2018.01) |

(52) U.S. Cl.
USPC ..... Plt./236
CPC ..... *A01H 6/00* (2018.05); *A01H 5/02* (2013.01); *A01H 6/28* (2018.05)

(58) Field of Classification Search
USPC ..... Plt./226, 236
See application file for complete search history.

(56) References Cited

PUBLICATIONS

Trademark to the name 'Kriya' for unprocessed hops, serial No. 88068180, filed Aug. 7, 2018.*

* cited by examiner

*Primary Examiner* — Anne Marie Grunberg
(74) *Attorney, Agent, or Firm* — Pepper Hamilton LLP

(57) ABSTRACT

A new *humulus* plant named 'Kriya' is disclosed. The leaves of this new *humulus* plant contain a cannabinoid level of ~15-23 mg/g and the inflorescence of this new *humulus* plant contain a cannabionoid level of ~124-142 mg/g.

4 Drawing Sheets

FIELD OF THE INVENTION

The present invention relates to a new and distinct *Humulus* plant. The plant is botanically known as *Humulus yunnanensis* var *kriya*.

BACKGROUND OF THE INVENTION

The new and distinct *humulus* plant originated from a cross hybridization of feral *H. yunnanensis* variants collected from the Pekong area within the Arunachal Pradesh region of India. Various *H. yunnanensis* samples were collected for analysis from various regions of India, including the groves in Puging, Singing, and Pekong, as well as in Mouling National Park, Kaying, and Lipo. *H. yunnanensis* male and female saplings with roots were collected, along with male and female flowers. All collected samples were tested for the presence of cannabinoids using standard methods known in the art (see Korte. F. and Sieper. H., J. Chromatoqr. 13:90 (1964), which is hereby incorporated by reference in its entirety). Only 5.2% of the *H. yunnanensis* samples collected had detectable levels of cannabinoids. The average cannabinoid level in the inflorescence of the *H. yunnanensis* plants containing cannabinoids was 2.1 mg/g[1].

[1] The cannabinoid level in plant tissue as described throughout this application is provided as milligrams of cannabinoid per gram of freeze dried plant material.

The Pekong strains of *H. yunnanensis* were identified as having unusually high cannabinoid content, with detectable levels of cannabigerol (CBG), cannabichromene (CBC), cannabidiol (CBD), cannabielsoin (CBE) and cannabidivarin (CBDV) found. The content of cannabidiol, cannabichromene and cannabigerol was high, usually >85-90% of the carboxylated cannabinoids and >65-70% of the uncarboxylated cannabinoids. No trace amounts of tetrahydrocannabinol were detected in the Pekong strains.

Table 1 (below) summarizes the inflorescence size and cannabinoid level of six of the *H. yunnanensis* plants collected from the Pekong region. The cannabinoid levels are reported as milligram cannabinoid per gram of freeze-dried plant tissue. Of these samples, samples 3, 4, and 6 were selected for breeding based on their high cannabinoid content. All of these samples were negative for the presence of tetrahydrocannabinol.

TABLE 1

Characteristics of Pekong *H. yunnanensis*

| | Pekong #1 | Pekong #2 | Pekong #3 |
|---|---|---|---|
| Inflorescence size (length in cm) | 3.7 cm | 4.8 cm | 7.4 cm |
| Inflorescence Cannabinoid (mg/g) | 22 mg/g | 26 mg/g | 56 mg/g |
| Leaf Cannabinoid (mg/g) | 6.3 mg/g | 6.3 mg/g | 7.5 mg/g |
| | **Pekong #4** | **Pekong #5** | **Pekong #6** |
| Inflorescence size (length in cm) | 6.2 cm | 5.9 cm | 6.6 cm |
| Inflorescence Cannabinoid (mg/g) | 41 mg/g | 32 mg/g | 42 mg/g |
| Leaf Cannabinoid (mg/g) | 5.3 mg/g | 6.1 mg/g | 4.8 mg/g |

To initiate the generation of 'Kriya', Pekong #3 plant was crossed with Pekong #6 plant to produce 128 female progeny. The cannabinoid level in female inflorescence of each plant was assessed. Of the 128 progeny, 74 of the plants did not contain a significant cannabinoid level. Twenty-three of the progeny had longer inflorescence (>6 cm), but the level of cannabinoid in the inflorescence was less than 20 milligrams per gram of freeze dried tissue. Twenty-four of the progeny had medium inflorescence (between 4 and 6 cm in length) and a medium inflorescence cannabinoid level (between 25 and 35 mg/g). Seven of the offspring had inflorescence greater than 7 cm in length and a cannabinoid level greater than 70 mg/g. From this analysis it was surmised that the presence of cannabinoids is a recessive trait in *Humulus yunnanensis*.

In parallel with the cross of Pekong #3 and Pekong #6, Pekong #3 was independently crossed with Pekong #4 plant to generate 128 progeny. The cannabinoid level in the female inflorescence was also assessed in these progeny. Eight plants having an inflorescence cannabinoid level between 66 mg/g and 73 mg/g were identified.

First generation plants produced by the cross between Pekong #3 and Pekong #6 and the cross between Pekong #3 and Pekong #4 having the highest cannabinoid level were selected for crossbreeding to produce second generation plants (n=7 plants from the Pekong #3/Pekong #6 cross; n=8 plants from the Pekong #3/Pekong #4 cross). The offspring of these crosses were bred to produce third and fourth generation offspring. The fifth generation yielded female plants having an average cannabinoid content of 128 milligrams cannabinoid per gram of freeze dried inflorescence and 16 milligrams cannabinoid per gram of freeze dried leaves and "trims". Of these female plants, one plant was chosen for asexual propagation. This new variety of high cannabinoid content plant was named *Humulus yunnanensis* var *kriya* or 'Kriya'.

Further propagation of female 'Kriya' was carried out using in-vitro culture starting on Mar. 14, 2017 in Nainital, Uttarakhand, India. The hypocotyl and the newly germinating buds of the female 'Kriya' plant were micro-propagated. Sterile plant tissues were removed from an intact plant. A small portion of plant tissue was placed on B5 medium to half its ionic strength (B5/2). The medium was thickened with agar to create a gel which supported the explant during growth.

The tissue samples produced during the first stage were multiplied to increase overall number. The tissue was grown into small "plantlets". Offshoot production was induced by hormone treatment. All propagules of 'Kriya' have been observed to be true to type in that during all asexual multiplication, the inflorescences and globose of the original plant have been maintained. After the formation of multiple shoots, these shoots were transferred to rooting medium with a high auxin\cytokinin ratio.

The 'Kriya' plantlets were transferred to the soil, with vermicompost, from the plant media. After a few days the plantlets were "hardened" and transferred to the field to grow to full maturity.

BRIEF DESCRIPTIONS OF THE DRAWINGS

FIG. 2A is a photograph of a seven-lobed 'Kriya' leaf and FIG. 2B is a drawing of a five-lobed 'Kriya' leaf.

Figure 4A:
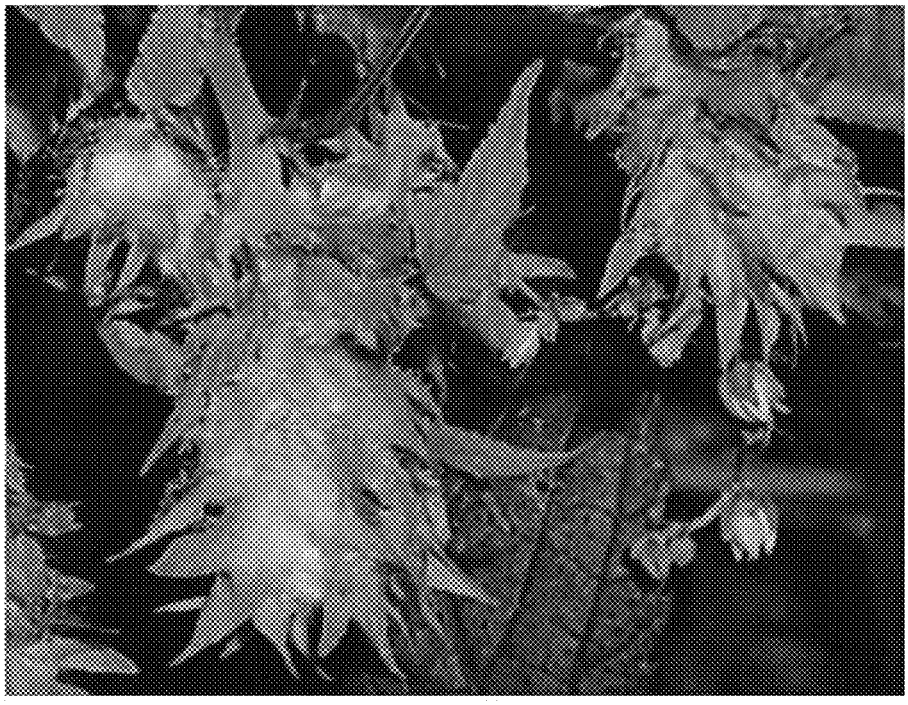
Figure 4B:
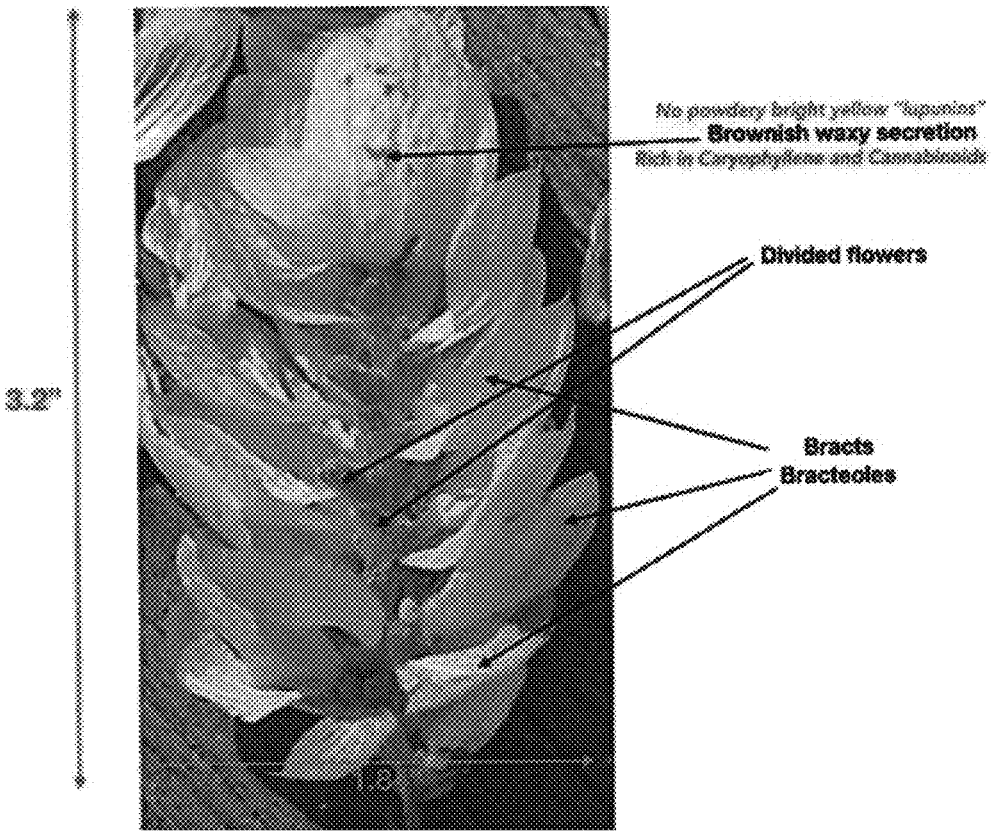

FIGS. 4A-4B are photographs of the *Humulus yunnanensis* var *kriya* inflorescence at different stages. FIG. 4A is a picture of a 'Kriya' inflorescence during the mid-vegetative growth state. FIG. 4B is a picture of a 'Kriya' inflorescence during the late reproductive stage.

DETAILED BOTANICAL DESCRIPTION

The present invention relates to a new and distinct *humulus* plant. The plant is botanically known as *Humulus yunnanensis* var *kriya*.

The following description of 'Kriya', unless otherwise noted, is based on observations made during June through November 2017. These measurements and ratings were taken from 'Kriya' plants planted in March 2017.

COMPARATIVE CANNABINOID CHARACTERISTICS

'Kriya' is distinguishable from its originating parents and other related varieties of *Humulus yunnanensis* based on the cannabinoid content in its leaves and inflorescence. Table 2 below details the number and type of *H. yunnanensis* samples collected from various regions in and around India, and the number of these samples that contained detectable levels of cannabinoids. As indicated in Table 2, many of the *H. yunnanensis* samples contained no detectable level of cannabinoids, i.e., *H. yunnanensis* plants collected from Ooty, Puging, Singing, Kaying, and Bomdeling did not contain detectable levels of cannabinoids.

TABLE 2

Comparison of Cannabinoid Content in Samples of *H. yunnanensis* Collected From India and Bhutan

| | Ooty[1] | | Puging[2] | |
|---|---|---|---|---|
| | Samples collected | Samples with Cannabinoids ("CB") | Samples collected | Samples w/CB |
| Flowers | 19 | 0 | 23 | 0 |
| Shoot tips | 11 | 0 | 18 | 0 |
| Leaves | 23 | 0 | 36 | 0 |
| Stem | 15 | 0 | 11 | 0 |
| Bark | 9 | 0 | 8 | 0 |
| Roots | 6 | 0 | 3 | 0 |
| Total Collected | 83 | | 99 | |
| Samples w/C8 | | 0 | | 0 |

| | Singing[3] | | Pekong[4] | |
|---|---|---|---|---|
| | Samples collected | Samples w/CB | Samples collected | Samples w/CB |
| Flowers | 41 | 0 | 69 | 14 |
| Shoot tips | 32 | 0 | 36 | 8 |
| Leaves | 67 | 0 | 103 | 13 |
| Stem | 24 | 0 | 43 | 0 |
| Bark | 20 | 0 | 29 | 0 |
| Roots | 8 | 0 | 15 | 0 |
| Total Collected | 192 | | 300 | |
| Samples w/C8 | | 0 | | 35 |

TABLE 2-continued

Comparison of Cannabinoid Content in Samples of *H. yunnanensis* Collected From India and Bhutan

| | Mouling[5] | | Kaying[6] | |
|---|---|---|---|---|
| | Samples collected | Samples w/CB | Samples collected | Samples w/CB |
| Flowers | 31 | 4 | 29 | 0 |
| Shoot tips | 23 | 2 | 21 | 0 |
| Leaves | 47 | 2 | 35 | 0 |
| Stem | 12 | 0 | 11 | 0 |
| Bark | 8 | 0 | 6 | 0 |
| Roots | 0 | 0 | 4 | 0 |
| Total Collected | 121 | | 106 | |
| Samples w/C8 | | 8 | | 0 |

| | Lipo[7] | | Bomdeling[8] | |
|---|---|---|---|---|
| | Samples collected | Samples w/CB | Samples collected | Samples w/CB |
| Flowers | 19 | 4 | 18 | 0 |
| Shoot tips | 14 | 2 | 14 | 0 |
| Leaves | 35 | 6 | 33 | 0 |
| Stem | 18 | 0 | 14 | 0 |
| Bark | 11 | 0 | 8 | 0 |
| Roots | 8 | 0 | 8 | 0 |
| Total Collected | 105 | | 100 | |
| Samples w/C8 | | 12 | | 0 |

| | Nanda Devi[9] | | |
|---|---|---|---|
| | Samples collected | Samples w/CB | % with CB |
| Flowers | 11 | 2 | |
| Shoot tips | 15 | 2 | |
| Leaves | 25 | 2 | |
| Stem | 8 | 0 | |
| Bark | 7 | 0 | |
| Roots | 2 | 0 | |
| Total Collected | 68 | | 1174 |
| Samples w/C8 | | 6 | 61 |
| | | | 5.20% |

Ooty[1]: Ooty village in Tamil Nadu, Southern India
Puging[2]: Puging village in Upper Siang district of Arunachal Pradesh India
Singing[3]: Singing village in Upper Siang district of Arunachal Pradesh India
Pekong[4]: Pekong village in Upper Siang district of Arunachal Pradesh India
Mouling[5]: Mouling National Park in Arunachal Pradesh India
Kaying[6]: Kaying village West Siang district of Arunachal Pradesh India
Lipo[7]: Lipo village West Siang district of Arunachal Pradesh India
Bomdeling[8]: Bomdeling Wildlife Sanctuary in Bhutan
Nanda Devi[9]: Nanda Devi National Park in Himachal Pradesh, India The presence of cannabinoids was most frequently detected in samples collected from the Pekong region. Table 1 above shows the cannabinoid levels in the six Pekong plants identified as having the highest cannabinoid levels, including the originating parent plants of 'Kriya'. Table 3 below shows average cannabinoid content in the inflorescence and leaves of first, second, third, and fourth generation[2] offspring of crossed Pekong samples, as well the average cannabinoid content in the inflorescence and leaves of 'Kriya'. The average cannabinoid level in 'Kriya' inflorescence is 133.5 mg/g±8.62 mg/g. This level is >2-fold higher than the inflorescence cannabinoid level of the original Pekong parental variants (41 mg/g-56 mg/g). This level is also significantly greater than the average inflorescence cannabinoid level found in first, second, third, and fourth generation plants.

First generation plants are progeny of the cross between Pekong #3 and Pekong #6 plants, and the progeny of Pekong #3 and Pekong #4 plants. Second generation plants are progeny of Pekong #3/Pekong #6 offspring crossed with Pekong #3/Pekong #4 offspring. Third generation plants are progeny of second generation crosses, and fourth generation plants are progeny of third generation crosses.

The average cannabinoid leaf content of 'Kriya' is 19.28±3.75 mg/g. This is also >2-fold higher than the leaf cannabinoid content of the originating Pekong parental variants (4.8 mg/g-7.5 mg/g). This level is also significantly greater than the average leaf cannabinoid level found in the first, second, third, and fourth generation plants.

Cannabidiol (CBD), cannabichromene (CBC), and cannabigerol (CBG) make up >98% of the cannabinoids present in the inflorescence and leaves of 'Kriya'. Trace amounts (<2%) of cannabielsoin (CBE) and cannbidivarin (CBDV) are also present. As with the parent strains, no tetrahydrocannabinol is present in 'Kriya'.

TABLE 3

Characteristics of '*Kriya*' and its Predecessors

| | Inflorescence Length | | | |
|---|---|---|---|---|
| Plant | N | Mean (cm) | Standard Deviation | Variance |
| 1st Generation | 76 | 5.767 | 1.325 | 1.755 |
| 2nd Generation | 62 | 5.933 | 1.294 | 1.675 |
| 3rd Generation | 47 | 6.15 | 1.319 | 1.739 |
| 4th Generation | 52 | 6.783 | 0.861 | 0.742 |
| *Humulus kriya* | 36 | 8.233 | 0.857 | 0.735 |

| | Inflorescence Cannabinoid | | | |
|---|---|---|---|---|
| Plant | N | Mean (mg/g) | Standard Deviation | Variance |
| 1st Generation | 76 | 33.167 | 8.06 | 64.967 |
| 2nd Generation | 62 | 34.667 | 8.335 | 69.467 |
| 3rd Generation | 47 | 46.334 | 7.23 | 52.267 |
| 4th Generation | 52 | 78.333 | 8.123 | 66.967 |
| *Humulus kriya* | 36 | 133.5 | 8.62 | 74.3 |

| | Leaf Cannabinoid | | | |
|---|---|---|---|---|
| Plant | N | Mean (mg/g) | Standard Deviation | Variance |
| 1st Generation | 83 | 1.78 | 0.342 | 0.117 |
| 2nd Generation | 73 | 2.24 | 0.623 | 0.388 |
| 3rd Generation | 48 | 3.4 | 0.678 | 0.46 |
| 4th Generation | 51 | 6.48 | 1.105 | 1.222 |
| *Humulus kriya* | 46 | 19.28 | 3.749 | 14.057 |

'Kriya' is also distinguishable from its originating parental plants based on average β-caryophyllene content in the inflorescence and leaves. The average β-caryophyllene level in 'Kriya' inflorescence is 53.11 mg/g±7.73 mg/g (milligrams of β-caryophyllene per gram of freeze-dried plant tissue). This level is >4-fold higher than the inflorescence β-caryophyllene level of the original Pekong parental variants (3 mg/g-11 mg/g). As shown in Table 4 below, the level of β-caryophyllene is also markedly different than the average inflorescence β-caryophyllene level found in first, second, third, and fourth generation plants.

The average β-caryophyllene leaf content of 'Kriya' is 10.63±1.99 mg/g. This is almost 10-fold higher than the leaf β-caryophyllene content of the originating Pekong parental variants (0.8 mg/g-1.6 mg/g). This level is also markedly different from the average leaf β-caryophyllene level found in the first, second, third, and fourth generation plants.

TABLE 4

β-Caryophyllene Content of 'Kriya' and its Predecessors

| | Inflorescence Beta Caryophyllene | | | |
|---|---|---|---|---|
| | N | Mean (mg/g) | Standard Deviation | Variance |
| 1st Generation | 76 | 26.77 | 6.41 | 41.11 |
| 2nd Generation | 54 | 28.52 | 4.80 | 23.06 |
| 3rd Generation | 63 | 36.52 | 7.81 | 61.08 |
| 4th Generation | 47 | 42.42 | 8.33 | 69.54 |
| *Humulus kriya* | 73 | 53.11 | 7.73 | 59.82 |
| | Leaf Beta Caryophyllene | | | |
| | N | Mean (mg/g) | Standard Deviation | Variance |
| 1st Generation | 67 | 2.09 | 0.411 | 0.168 |
| 2nd Generation | 73 | 2.77 | 0.52 | 0.28 |
| 3rd Generation | 59 | 4.17 | 0.54 | 0.29 |
| 4th Generation | 71 | 7.9 | 1.87 | 3.49 |
| *Humulus kriya* | 82 | 10.63 | 1.99 | 3.98 |

'Kriya' is also distinguishable from its originating parental plants based on average inflorescence size. As indicated in Table 3 above, the average length of the inflorescence of 'Kriya' is 8.233±0.875 cm, which is distinctly longer than the size of the inflorescence of the originating parent plants (range 6.2 cm-7.4 cm).

BOTANICAL DESCRIPTION

The following botanical description of the new *humulus* cultivar will vary somewhat depending upon cultural practices and climatic conditions, and can vary with location and season. Quantified measurements are expressed as an average of measurements taken from a number of individual 'Kriya' plants. The measurements of any individual plant or any group of plants of the new cultivar may vary from the stated average. The color chart used was The Royal Horticulutural Society Colour Chart ($5^{th}$ ed. 2007).

Figure 1:
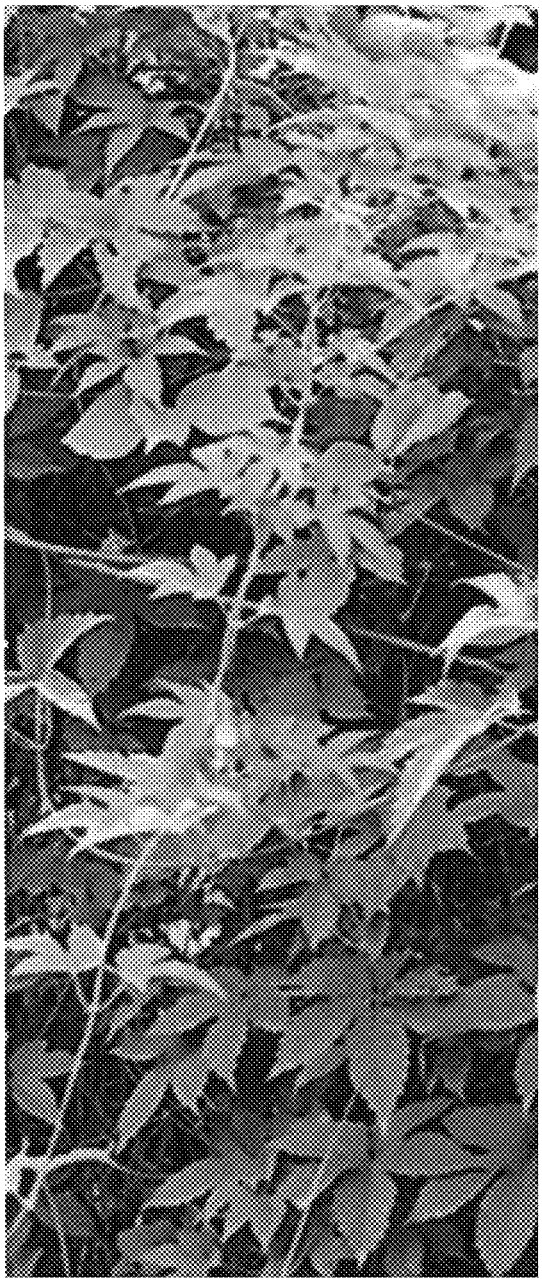
FIG. 1 is a photograph of the 'Kriya' plant growing in a greenhouse in Ooty, India in July 2017.
Figure 2A:
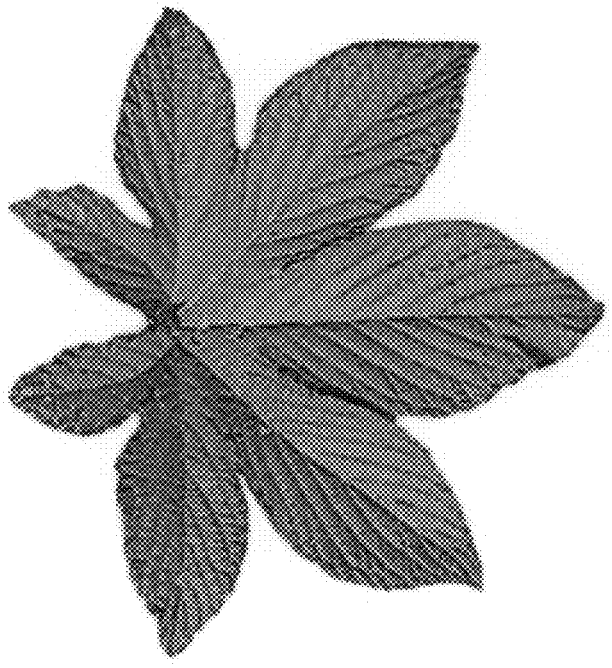
FIGS. 2A-2B show the *Humulus yunnanensis* var *kriya* leaf.
Figure 2B:
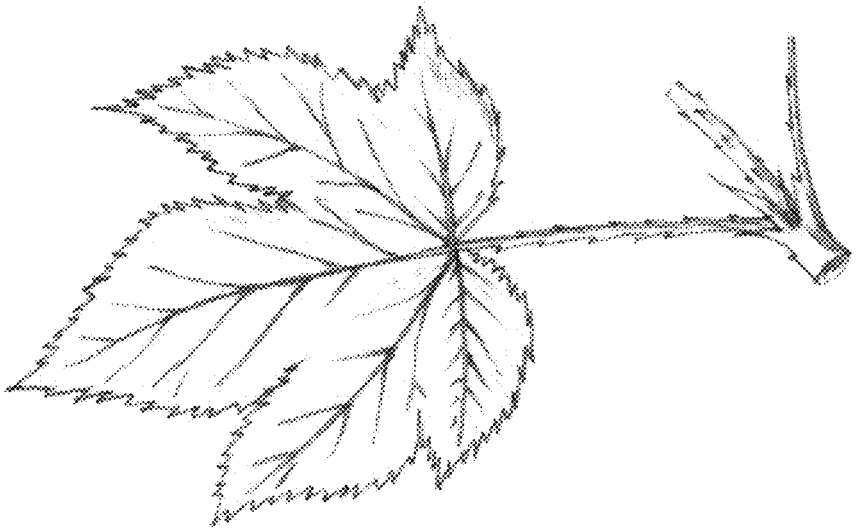
Figure 3:
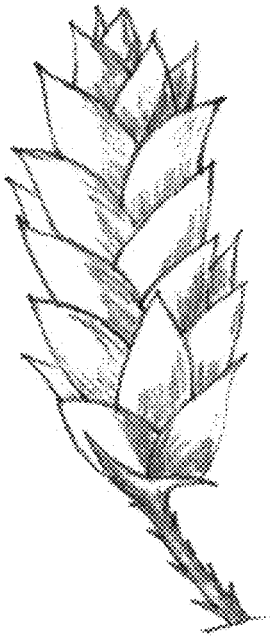
FIG. 3 is a drawing of a young *Humulus yunnanensis* var *kriya* female inflorescence.

'Kriya' is a perennial vine that is 4-8 feet long, branching occasionally (see FIG. 1). The twining habit of 'Kriya's' stems allow this vine to climb adjacent vegetation and fences. The rather stout stems are light green and longitudinally ridged. Along the ridges of each stem, there are rows of stiff prickly hairs. A pair of opposite leaves occur at intervals along each stem.

The plant has dormant stage (December-February) where the plant sheds all its leaves and only the dried pods remain. The dormant stage is followed by a growth stage (February-May), a vegetative stage (June-August), and flowering stage (August-October), after which the plant starts gradually going dormant again. As referred to herein, a "young" plant refers to a plant in the early growth stage (i.e., February to May), and a "mature" plant refers to a plant at the late flowering stage (i.e., August to October).

'Kriya's' leaves are opposite and cordite, and can grow up to 6 inches long and 6 inches wide. The leaves are palmate, generally divided into 5 lobes with toothed margins; however leaves containing 7 and 9 lobes have been observed. Upper leaves are normally 3 lobed and develop to five to seven lobes as they mature. Each lobe is oblanceolate or elliptic in shape with coarsely serrated margins. The upper surface of each leaf is medium green and moderately covered with short rough hairs (subglabrous and membranous). The lower surface has stiff prickly hairs along the major veins.

'Kriya' normally grows to cover large areas of open ground. It overgrows shrubs and small trees and can choke them off. It grows rapidly in summer and forms dense foliage several feet deep. It twines around shrubs and trees causing them wither. It can displace native vegetation. It is a bushy vine that can be trained to be conical. It takes a conical appearance when it climbs a trellis or a small tree.

The normal adaxial surface of the leaves are normally subglabrous and membranous. The normal leaf isn't blistered or curled. During a humid and rainy growing season and cases of "Downy Mildew" caused by *Pseudoperonospora humuli* have been observed. The infected leaves become brittle and have downward curling leaves. A yellow color affects the infected leaves and the spores then appear as purple to black blotches on the abaxial (underside) of infected leaves.

The rather stout petioles of 'Kriya' are as long as, or a little shorter than, the leaves. These petioles are light green and covered with stiff downward pointing prickly hairs.

The young female 'Kriya' inflorescence is a short spike of flowers with bracts and bracteoles that are ovate-orbiculate. This spike becomes globose and large with age and tends to nod downward, spanning about 5-10 cm long. Flowers originate as pistillate bracts in the leaf axils. The appearance of each spike is dominated by several overlapping pistillate bracts. At the base of each bract, there is a pair of inconspicuous female flowers. Initially, the pistillate bracts are narrowly deltoid in shape, but enlarge in size to 6-9 mm long and become deltoid with recurved tips and are pilose. These bracts are light to dark green, hairy, and strongly ciliate along their smooth margins. These bracts turn a yellowish brown when mature (see FIG. 4). The bracteoles are more prominent in the young plant, and do not have a flower at the base. Each female flower has a divided style and an inconspicuous calyx that surrounds the developing ovary; there are no petals (see FIG. 4).

The mature female inflorescences are leafy cone-like catkins or strobiles. As noted above, when fully developed, the strobiles are about 5-10 cm long, oblong in shape and rounded, consisting of a number of overlapping, green bracts, attached to a separate axis. If these leafy bracts are removed, the axis will be seen to be hairy and to have a zigzag path (see FIG. 4). Each of the bracts enfolds at the base a small fruit (achene). The fruit is an ovoid achene which is about ¼ inch in diameter, roundish, rough, light brown and speckled. The fruit and bract have translucent glands, which secrete a waxy substance. 'Kriya' does not secrete the powdery Lupulin which gives the "hops" plant (*Humulus lupulus*) its distinctive flavor.

Disease susceptibility: Aphids, spidermites, powdery mildew, downy mildew, black root rot, hop mosaic virus, and apple mosaic virus.

Aroma: Woody aroma, soft complex spice, mild cananga/cinnamon.

Use: Medicinal.

Time of flowering: Single flowering season; Autumn.

Leaves:

*Leaf arrangement*.—Opposite.

*Immaure leaf shape*.—Cordate.

*Mature leaf shape*.—Usually a palmate shape, lobed (5-7 lobes). Sometimes simple leaf, also lobed.

*Leaf apex shape*.—Acutely acuminate.
*Leaf base shape*.—Cordate.
*Abaxial surface*.—Rigid spinulose hairs on veins.
*Abaxial surface color*.—140D young plant; 140A mature plant.
*Adaxial surface*.—Densely pubescent.
*Adaxial surface color*.—129D young plant; 130C mature plant.
*Margin*.—Serrate.
*Average length*.—5-15 cm.
*Average width*.—4-15 cm.
*Cannabinoid content*.—15-23 mg/g.

Petiole:
*Average petiole length*.—4-10 cm.
*Average diameter*.—5 mm.
*Average circumference*.—2 cm.
*Color*.—185A.

Inflorescence: Leafy cone-like catkins or strobiles.
*Arrangement*.—Spicate.
*Shape*.—Ovaloid.
*Average length*.—5-10 cm.
*Average width*.—2-4 cm.
*Strobiles*.—Color 153D, 153C, 153B, 153A, 152D, 152C, 152B.
*Bracts and bracteole*.—Subglabrous and membraneous; abaxial surface has prominent veins. shape: initially narrowly deltoid; with maturation become enlarged and deltoid with recurved tips. size: 1.5 cm to 3 cm. color: immature bract is light to dark green 140D, 140C, 140B, 140A, mature bract is yellowish brown, 162D, 162C, 162B, 162A. bract apex length: 0.05-0.80 inch.
*Cones per node at the side shoot*.—Middle of the plant: 1-3 cones. Upper third portion of the plant: 0-1 cones.
*Total cones per side shoot*.—Middle of the plant: 4-16 cones. Upper third portion of the plant: 0-7 cones.
*Total cones per plant*.—220-840.
*Achene*.—Size: 3 to 9 cm. Shape: flat. Color: 200D.
*Cannabinoid content*.—124-142 mg/g.
*Flowers*.—Color: 149D, 149C.
*Main shoot anthocyanin coloration*.—144C, 144B.

What is claimed:

1. A new and distinct *humulus* plant as illustrated and described herein.

* * * * *